United States Patent [19]

Kasafírek et al.

[11] Patent Number: 4,898,930
[45] Date of Patent: Feb. 6, 1990

[54] PEPTIDE DERIVATIVES AND PROCESSES FOR THEIR PREPARATION

[75] Inventors: Evžen Kasafírek; Miroslav Rybák; Ivan Krejcí; Antonín Sturc; Alena Roubalová, all of Prague; Jiří Vanžura, Hradec Králové; Evžen Křepela, Brno; Michal Bartík, Kosice, all of Czechoslovakia

[73] Assignee: Spofa, spojene podniky pro, Prague, Czechoslovakia

[21] Appl. No.: 62,300

[22] Filed: Jun. 12, 1987

[30] Foreign Application Priority Data

Jun. 12, 1986 [CS] Czechoslovakia .................... 4332-86

[51] Int. Cl.$^4$ ................................................ C07K 7/54
[52] U.S. Cl. ................................... 530/332; 530/323; 562/503; 562/507; 560/125; 560/129; 564/159; 548/537
[58] Field of Search ............................... 530/330, 331; 260/998.2; 550/317, 323, 321, 332; 562/503, 507; 560/125, 129; 564/159; 548/537

[56] References Cited

U.S. PATENT DOCUMENTS 4,278,595  7/1981  Cort ..................................... 530/312
4,620,012  10/1986 Henning et al. ..................... 548/411
4,690,936  9/1987  Ryan et al. .......................... 514/362

OTHER PUBLICATIONS

Inhibition of Proliferative Activity by Cyclic Dipeptides: Spirocyclic Derivatives of 1-Aminocyclopentane-Carboxylic Acid (Toxicology Letters, 31 (1986) 189–192).
VIIIth International Symposium on Medicinal Chemistry (Proceedings), vol. 2; Swedish Academy of Pharmaceutical Sciences.
Activitas Nservosa Superior—vol. 28, 12/86, Research Institute For Pharmacy and Biochemistry.

Primary Examiner—Delbert R. Phillips
Assistant Examiner—T. Wessendorf
Attorney, Agent, or Firm—Klein & Vibber

[57] ABSTRACT

Peptide ester and amide derivatives of the general formula I:

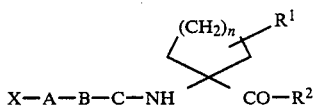

in which X is H or an acyl, A and B are structurally defined amino acid residues, n is an integer of from 1 to 3, $R^1$ is H or a lower alkyl and either $R^2$ or C is a defined optionally modified amino acid residue and the other is a lower alkoxyl, an amino group or a direct chemical bond, are converted under physiologic conditions, by enzymic hydrolysis in pathologically altered tissues and subsequent spontaneous cyclization, into pharmacodynamically active spirocyclic peptide derivatives of the general formula III:

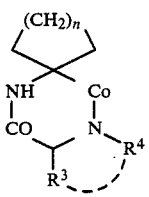

in which $R^3$ and $R^4$ are H atoms, optionally substituted alkyl groups or jointly an aliphatic chain forming preferably a 2,5- piperazinedione ring, and hence can act as pro-farmaca (drug precursors) of prolonged biological effect.

15 Claims, No Drawings

PEPTIDE DERIVATIVES AND PROCESSES FOR THEIR PREPARATION

FIELD OF THE INVENTION

The invention relates to peptide derivatives of the general formula I:

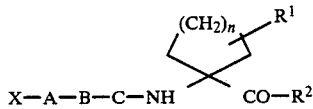

in which
X is H, a $C_2$ to $C_5$ alkanecarbonyl, a $C_3$ to $C_6$ carboxyalkanecarbonyl or a p-toluenesulfonyl,
A is a glycine, alanine, leucine, phenylalanine, tyrosine, lysine or arginine residue,
B is a glutamine, proline, arginine or lysine residue or a direct chemical bond,
n is an integer of from 1 to 3, $R^1$ is H or a $C_1$ to $C_3$ alkyl and
$R^2$ is a $C_1$ to $C_3$ alkoxyl or an amino group when C is a peptidically bound glycine, alanine, leucine, phenylalanine, glutamine or serine residue or $R^2$ is a peptidically bound glycine, alanine, leucine, phenylalanine or serine methyl ester, ethyl ester or amide residue when C is a direct chemical bond.

The subject peptides are of possible interest since under the action of proteolytic enzymes present in pathological tissues they decompose to give C-terminal peptide esters or amides of the general formula II:

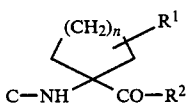

in which n and $R^1$ are the same as in formula I and $R^2$ is as defined above when respectively C is an aforementioned amino acid residue or alternatively a hydrogen atom. These peptide derivatives cyclize spontaneously and so afford spirocyclic peptides of the general formula III:

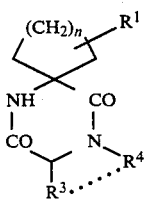

in which n and $R^1$ is the same as in formula I, $R^3$ is H, a methyl, an isobutyl, a 2-aminoethyl, a 2-hydroxyethyl or a benzyl and $R^4$ is a hydrogen atom or $R^3$ jointly with $R^4$ form a di-, tri- or tetramethylene chain.

DESCRIPTION OF THE PRIOR ART

Spirocyclic peptides of formula III are partly known, partly new. They are pharmacodynamically active substances that influence different biological systems. Thus, cyclo (L-alanyl-1-amino-1-cyclopentanecarbonyl) shows remarkable effects on the environmental behavior of experimental animals (see I. Krejci et al., Activitas Neurosa Superior) and in certain other pharmacological tests (see Czechoslovak Author Certificate No. 231,227).

Said spirocyclic peptides are comparatively less soluble, which is disadvantageous in preparing medicinal dosage forms.

A possible route to overcoming the above obstacle is based on preparing a sufficiently soluble, more hydrophilic precursor compound comprising an additional optionally modified amino acid or lower peptide moiety and affording under pathophysiological conditions, by enzymic cleavage in the affected tissue (e.g. infected or inflammated), the respective pharmacodynamically active substance, which is thus immediately liberated in or safely conveyed to the target organ in an amount substantially corresponding to the actual requirement of the organisms without adverse sequels of possible overdosage and, due to its gradual liberation, elicits the desired effect over a prolonged time period.

OBJECT OF THE INVENTION

According to the present invention, the goal of safe efficient and economical medication with said spirocyclic compounds of formula III is attained with the use of the subject peptide derivatives of formula I in the quality of drug precursors (pro-drugs). The intact, non-cleaved peptide derivative of formula I is physiologically inert and under nonpathological conditions is metabolized and eliminated from the organism without liberating biologically active substances or leaving undesirable residue in healthy tissues.

Said pathophysiological cleavage of the subject peptide derivatives of formula I is effected at bodily temperature and pH either under the action of certain pure proteolytic enzymes (proteases), e.g. trypsine, kallikrein, chymotrypsine, cathepsin G, thrombin, plasmin or "factor X", as well as aminopeptidases, e.g. leucinaminopeptidase, or aminodipeptidyl-peptidases, e.g. the DAP IV peptidase, or also under the action of native, endogenous enzymic systems of brain, liver, kidney, pancreas, lungs, heart or intestine tissues or of blood serum.

The spontaneous cyclization of the so liberated intermediary compounds of formula II to give said pharmacodynamically active spirocyclic peptide 2,5-piperazinedione derivatives of formula III proceeds at similar mild conditions in the pathologically affected tissue during a period of about from 4 to 12 hours.

DETAILED DESCRIPTION OF THE INVENTION

The above cleavage mechanism was demonstrated in vitro by thin-layer chromatography in n-butanol-acetic acid-water 4:1:1 for cleaving ethyl leucyl-alanyl-1-amino-1-cyclopentanecarboxylate ($R_f$ 0.44) with leucinaminopeptidase (LAP) in "tris" (abbreviated name for tris(hydroxymethyl)aminomethane buffer of pH 7.4 at 37° C. The formed ethyl alanyl-1-amino-1-cyclopentanecarboxylate ($R_f$ 0.16) cyclizes spontaneously to afford cyclo (alanyl-1-amino-1-cyclopentanecarbonyl) ($R_f$ 0.64). This two-stage conversion of the starting peptide derivative into the spirocyclic product proceeds markedly even after two hours of incubation. A similar evidence was also obtained for other peptides and other enzymic systems. Thus, ethyl N-acetyltyrosyl-alanyl-1-amino-1-cyclopentanecarboxylate, ethyl 3-carboxypropionylphenylalanyl-phenylalanyl-1-amino-1-cyclopentanecarboxylate and N-acetyltyrosyl-1-amino-1-cyclopentanecarbonylserine methyl ester were cleaved with chymotrypsine, and ethyl glycyl-prolyl-alanyl-1-amino-1-cyclopentanecarboxylate was similarly cleaved with DAP IV. Comparable results were obtained with the use of native tissue extracts with enzymic activity in place of the above mentioned pure enzymes.

The structural design of the subject peptide derivatives of formula I was primarily focused on desired negligible toxic properties and physiological aspects of administration. Therefore, the corresponding esters with Et (an ethyl) as the C-terminal protective group were preferred, and conversion of the products into appropriate acid addition salts, predominantly citrates, was found advantageous. The preparative strategy was chosen so as to facilitate the cyclization of the intermediary compounds into the biologically active spirocyclic peptide derivatives.

The subject compounds of the general formula I are available by conventional methods of the preparative chemistry of peptides. A suitable route for preparing the subject compounds consists principally in reacting a peptide derivative of the general formula IV:

in which A and B are the same as in formula I, Y is a $C_2$ to $C_5$ alkanecarbonyl or a protective group such as a benzyloxycarbonyl or a tert-butyloxycarbonyl and W is a carboxyl activating moiety such as a reactive halogen atom or an anhydride or reactive ester function, with a peptide derivative of the general formula II, in which n, $R^1$, $R^2$ and C are as defined herein, subsequent deprotecting of the so obtained peptide derivative and isolation of the liberated product, whereupon, if required, the product is converted into an acid addition salt or acylated.

A convenient alternative route to the subject compounds of formula I consists in reacting a peptide derivative of the general formula V:

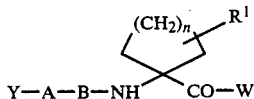

in which A, B, n, and $R^1$ are the same as in formula I and Y and W are the same as in formula IV, with glycine, alanine, leucine, phenylalanine or serine methyl ester, ethyl ester or amide and subsequent deprotection, isolation and optional salt formation or acylation.

Said acylation step is effected with the use of a reactive derivative of a carboxylic acid of the general formula X—COOH in which X is the same as in formula I, preferably with an acid anhydride or halide thereof.

Starting materials required for the preparation are known substances available by methods described in the pertinent literature.

Further particulars of the procedure are illustrated by the subsequent non-limitative examples. Melting points were determined on Kofler and are not corrected. Analytical samples were dried at 70 Pa. Optical rotations: Perkin-Elmer 141 polarimeter, Chromatography on silica gel ("Kieselgel" Merck) thin layer in 1-BuOH-AcOH-water 4:1:1 ($S_1$) and 1-BuOH-AcOH-pyridine-water 15:3:10:6 ($S_2$) systems. Evaporation of solution was done on a rotary vacuum evaporator.

EXAMPLES OF PREFERRED EMBODIMENTS OF THE INVENTION

EXAMPLE 1

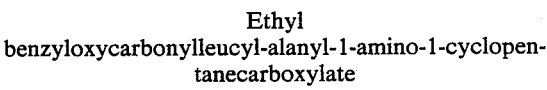

To a solution of benzyloxycarbonylleucyl-alanine (6.72 g, 20 mmoles) in dimethylformamide (70 ml) was added N-hydroxysuccinimide (2.3 g. 20 mmoles) and on cooling to −5° C. N,N'-dicyclohexyl-carbodiimide (4.4 g) was admixed. After 1 hour of stirring and cooling (−5° C.) there was added a dimethylformamide (40 ml) solution of ethyl 1-amino-1-cyclopentanecarboxylate liberated from its hydrochloride (3.86 g, 20 mmoles) with N-ethylpiperidine (2.8 ml) and the reaction mixture was stirred for further 2 hours at room temperature. After subsequent 12 hours of standing, the N,N'-dicyclohexylurea precipitate was filtered off, washed with dimethylformamide and the filtrate was evaporated. The residue was dissolved in an ethyl acetate-water mixture and the organic phase was shaken successively with 1M hydrochloric acid, water, 5% sodium hydrogencarbonate and water, dried over anhydrous sodium sulfate and evaporated. The residue was crystallized from ethyl acetate (25 ml) and petroleum ether (200 ml) to give 7.6 g (80%) of the title compound, m.p. 102° to 104° C., after similar recrystallization 104° to 106° C. $[\alpha]_D^{20} - 35.9°$ (c 0.2, methanol).

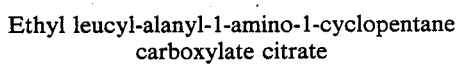

To a solution of the preceding ester (7.5 g, 15.8 mmoles) in methanol (100 ml) was added a suspension of 5% Pd/C catalyst (0.8 g) in toluene (30 ml). Hydrogenolysis was conducted at room temperature in an autoclave at an initial hydrogen pressure of 2 MPa and stirrer speed of 2000 r.p.m. After 10 minutes, the autoclave was degased, the catalyst was filtered off and the filtrate was evaporated. The residue was dissolved in methanol (30 ml) and a solution of citric acid (3.3 g) in methanol (20 ml) was added. The resulting solution was mixed gradually with 300 ml of ether, and after 2 hours of standing, the citrate precipitate was separated, washed with ether and dried in a desiccator over phosphorus pentoxide to give 4.7 g of the title product, $R_f$ 0.44/$S_1$, 0.58/$S_2$ $[\alpha]_D^{20} - 10.9°$ (c 0.2, MeOH).

Similar procedures afforded the following compounds:

Ethyl benzyloxycarbonylalanyl-alanyl-1-amino-1-cyclopentane carboxylate, yield 76%, m.p. 134° to 136° C. (ethyl acetate-petroleum ether). $[\alpha]_D^{20} - 39.2°$ (c 0.2, methanol).

Ethyl alanyl-alanyl-1-amino-1-cyclopentanecarboxylate citrate, m.p. 99° to 102° C., $R_f$ 0.40/$S_1$, 0.56/$S_2$. $[\alpha]_D^{20} - 14.8°$ (c 0.2, MeOH).

Methyl benzyloxycarbonylalanyl-alanyl-1-amino-1-cyclobutanecarboxylate, m.p. 101° to 103° C., $[\alpha]_D^{20} - 43.0°$.

Methyl alanyl-alanyl-1-amino-1-cyclobutanecarboxylate citrate, $R_f$ 0.27/$S_1$, 0.52/$S_2$. $[\alpha]_D^{20} - 12.9°$.

Ethyl benzyloxycarbonylalanyl-alanyl-1-amino-1-cyclohexanecarboxylate, m.p. 110° to 112° C. $[\alpha]_D^{20} - 42.2°$.

Ethyl alanyl-alanyl-1-amino-1-cyclohexanecarboxylate citrate, $R_f$ 0.37/$S_1$, 0.68/$S_2$ $[\alpha]_D^{20} - 42.2°$.

Ethyl benzyloxycarbonylphenylalanyl-phenylalanyl-1-amino-1-cyclopentanecarboxylate, m.p. 93° to 96° C. (toluene-petroleum ether). $[\alpha]_D^{20} -22.5°$.

Ethyl phenylalanyl-phenylalanyl-1-amino-1-cyclopentanecarboxylate citrate, $R_f$ 0.64/$S_1$, 0.78/$S_2$. $[\alpha]_D^{20} -4.7°$.

Additionally prepared compounds of the invention and intermediates:

Ethyl tert-butyloxycarbonyl-$N^g$-nitroarginyl-alanyl-1-amino-1-cyclopentanecarboxylate (please note: $N^g$-guanidine N atom in the arginine residue), by the carbodiimide technique using N-hydroxysuccinimide from $N^{alpha}$-tert-butyloxycarbonyl-$N^g$-nitroarginine and ethyl alanyl-1-amino-1-cyclopentanecarboxylate hydrobromide, m.p. 112° to 115° C. (ethyl acetate), $[\alpha]_D^{20}$ 20.4° (c 0.2, MeOH).

Ethyl acetylleucyl-$N^g$-nitroarginyl-alanyl-1-amino-1-cyclopentanecarboxylate, similarly from N-acetylleucine and ethyl $N^g$-nitroarginyl-alanyl-1-amino-1-cyclopentanecarboxylate hydrochloride (yield 69%), m.p. 223° to 225° C. (aqueous ethanol), $R_f$ 0.33/$S_1$, 0.69/$S_2$, $[\alpha]_D^{20} -11.8°$ (c 0.2, dimethylformamide).

Methyl acetylleucyl-$N^{epsilon}$-benzyloxycarbonyllysyl-alanyl-1-amino-1-cyclopentanecarboxylate, similarly from N-acetylleucine and methyl $N^{epsilon}$-benzyloxycarbonyllysyl-alanyl-1-amino-1-cyclopentanecarboxylate hydrochloride (yield 72%), m.p. 202° to 204° C., $R_f$ 0.52($S_1$, 0.63)$S_2$, $[\alpha]_D^{20} -41.6°$ (c 0.2, MeOH).

Ethyl acetylleucyl-arginyl-alanyl-1-amino-1-cyclopentanecarboxylate acetate, by pressure hydrogenolysis (6 MPa) deprotection from the corresponding $N^g$-nitroarginyl analog (yield 78%), m.p. 203° to 205° C. (methanol-ethyl acetate), $[\alpha]_D^{20} -32.1°$ (c 0.2, MeOH).

Methyl acetylleucyl-lysyl-alanyl-1-amino-1-cyclopentanecarboxylate acetate, similarly by hydrogenolysis (2 MPa) of the corresponding benzyloxycarbonyl derivative (yield 85%), m.p. 210° to 212° C. (methanol-ethyl acetate), $[\alpha]_D^{20} -47.1°$ (c 0.2 MeOH).

In place of methanol-ethyl acetate, also MeOH-AcOEt can be written (Ac-acetyl, Et-ethyl).

EXAMPLE 2

Benzyloxycarbonylglycyl-prolyl-alanine methyl ester

To a solution of benzyloxycarbonylglycyl-proline pentachlorophenyl ester (5.55 g, 10 mmoles) in dimethylformamide (30 ml) was added alanine methyl ester liberated from its hydrochloride (1.4 g, 10 mmoles) with N-ethylpiperidine (1.4 ml). After 5 hours of a stirring and 12 hours of standing at room temperature the solution was evaporated, the residue was taken into ethyl acetate and the organic phase was washed successively with 1M hydrochloric acid, water, 5% sodium hydrogencarbonate and water, dried over anhydrous sodium sulfate and evaporated. The residue was crystallized from ethyl acetate-petroleum ether to give 1.95 g (50%) of the title product, m.p. 103° to 106° C. An analytical sample was recrystallized similarly, m.p. 105° to 108° C. $[\alpha]_D^{20} -100.1°$ (c 0.2, MeOH).

Benzyloxycarbonylglycyl-prolyl-alanine, by alkaline hydrolysis of the preceding ester, yield 79%, m.p. 144° to 145° C. (methylene chloride-petroleum ether). $[\alpha]_D^{20} -95.6°$.

Ethyl benzyloxycarbonylglycyl-prolyl-alanyl-1-amino-1-cyclopentane-carboxylate, by the procedure of example 1 from the preceding compound and ethyl 1-amino-1-cyclopentanecarboxylate, yield 78%, $[\alpha]_D^{20} -61.5°$ Ethyl glycyl-prolyl-alanyl-1-amino-1-cyclopentanecarboxylate citrate, by hydrogenolytic deprotection of the preceding, m.p. 115° to 118° C. $R_f$ 0.22/$S_1$, 0.58/$S_2$. $[\alpha]_D^{20} -62.7°$.

EXAMPLE 3

Ethyl 3-carboxypropionylphenylalanyl-phenylalanyl-1-amino-1 cyclopentanecarboxylate A solution of ethyl benzyloxycarbonylphenylalanyl-phenylalanyl-1-amino-1-cyclopentanecarboxylate (590 mg, 1 mmole) in methanol was hydrogenated by the procedure of Example 1. The methanolic solution was evaporated, dissolved in tetrahydrofurane, evaporated and acylated with glutaric anhydride (175 mg) in dimethylformamide for 2 hours at 80° C. The reaction mixture was evaporated and the product was precipitated with water to give the title compound, m.p. 193° to 196° C. (dimethylformamide-water).

EXAMPLE 4

N,O-Diacetyltyrosyl-alanine methyl ester

To a solution of N,O-diacetyltyrosine (13.3 g, 50 mmoles) and N-ethylpiperidine (7 ml) in tetrahydrofurane (100 ml) precooled to $-15°$ C. was added ethyl chloroformate (5 ml). After 15 minutes of stirring and cooling ($-15°$ C.) alanine methyl ester liberated from its hydrochloride (7.0 g, 50 mmoles) with N-ethylpiperidine (7 ml) was admixed. After 2 hours of stirring at 0° C. and 12 hours of standing at room temperature, the solution was evaporated, the residue was taken into ethyl acetate and the organic phase was successively washed with 1M hydrochloric acid, water, 5% sodium hydrogencarbonate and water, dried over anhydrous sodium sulfate and evaporated. Crystallization from 2-propanol-petroleum ether yielded 10.6 g (60%) of the title product. An analytical sample was recrystallized similarly, m.p. 173° to 176° C. $[\alpha]_D^{20} -7.5°$.

N-Acetyltyrosyl-alanine

The preceding protected ester (7 g, 20 mmoles) dissolved in methanol (100 ml) was hydrolyzed for 1 hour with 2M sodium hydroxide (25 ml). The reaction mixture was processed in the known manner to given an amorphous product. $R_f$ 0.59/$S_1$, 0.67/$S_2$.

Ethyl N-acetyltyrosyl-alanyl-1-amino-1-cyclopentanecarboxylate, by the procedure of Example 1 from the preceding compound and ethyl-1-amino-1-cyclopentanecarboxylate, yield 88%, m.p. 168° to 171° C., $[\alpha]_D^{20} -3.1°$ (c 0.2, MeOH).

Similar procedures afford the following compounds:

Ethyl tert-butyloxycarbonylglutaminyl-1-aminocyclopentanecarboxylate, from tert-butyloxycarbonylglutamine and ethyl 1-amino-1-cyclopentanecarboxylate, yield 62%, m.p. 131° to 132° C.

Ethyl glutaminyl-1-amino-1-cyclopentanecarboxylate hydrochloride, by deprotection of the preceding compound with hydrogen chloride in glacial acetic acid. $R_f$ 0.38/$S_1$, 0.44/$S_2$.

Ethyl $N^{alpha}$-tert-butyloxycarbonyl-$N^{omega}$-benzyloxycarbonyllysyl-glutaminyl-1-amino-1-cyclopentanecarboxylate, by the anhydride technique from the respective protected lysine compound and the preceding dipeptide ethyl ester, yield 93%, m.p. 127° to 130° C.

Ethyl $N^{omega}$-benzyloxycarbonyllysyl-glutaminyl-1-amino-1-cyclopentane-carboxylate hydrochloride, by analogous deprotection of the preceding compound $R_f$ 0.28/$S_1$, 0.63/$S_2$.

Ethyl acetylleucyl-$N^{omega}$-benzyloxycarbonyllysyl-glutaminyl-1-amino-1-cyclopentanecarboxylate, by the carbodiimide technique in the presence of N-hydroxysuccinimide from N-acetylleucine and the corresponding tripeptide ethyl ester in dimethylformamide, m.p. 231° to 232° C. (aqueous dimethylformamide).

Ethyl acetylleucyl-lysyl-glutaminyl-1-amino-1-cyclopentanecarboxylate acetate, by hydrogenolytic deprotection of the preceding derivative, after crystallization from methanol-ether $R_f$ 0.24/$S_1$, 0.51/$S_2$.

Ethyl $N^{alpha}$-tert-butyloxycarbonyl-$N^{omega}$-benzyloxy carbonyllysyl-glycyl-1-amino-1-cyclopentanecarboxylate, by the anhydride technique from the respective protected lysine and ethyl glycyl-1-amino-1-cyclopentanecarboxylate hydrobromide, $R_f$ 0.41/$S_1$, 0.72/$S_2$.

Ethyl $N^{omega}$-benzyloxycarbonyllysyl-glycyl-1-amino-1-cyclopentanecarboxylate hydrochloride, by analogous deprotection of the preceding compound as above. $R_f$ 0.28/$S_1$, 0.63/$S_2$.

Ethyl acetylleucyl-$N^{omega}$-benzyloxycarbonyllysyl-glycyl-1-amino-1-cyclopentanecarboxylate, from N-acetylleucine and the preceding tripeptide ethyl ester in dimethylformamide, m.p. 179° to 182° C. (aqueous dimethylformamide).

Ethyl acetylleucyl-lysyl-glycyl-1-amino-1-cyclopentanecarboxylate acetate, by hydrogenolytic deprotection of the preceding compound, after crystallization from methanol-ether $R_f$ 0.25/$S_1$, 0.54/$S_2$.

Methyl N,O-diacetyltyrosyl-1-amino-1-cyclopentanecarboxylate, by the anhydride technique from N,O-diacetyltyrosine and methyl 1-amino-1-cyclopentanecarboxylate, yield 43%, m.p. 210° to 212° C. (ethanol).

N-Acetyltyrosyl-1-amino-1-cyclopentanecarboxylic acid, by alkaline hydrolysis of the preceding ester, m.p. 252° to 254° C. (aqueous ethanol).

N-Acetyltyrosyl-1-amino-1-cyclopentanecarbonylserine methyl ester, similarly from the preceding acid and serine methyl ester, m.p. 128° to 132° C. (2-propanol-petroleum ether), $[\alpha]_D^{20}+8.6°$.

EXAMPLE 5

Ethyl benzyloxycarbonylalanyl-glycyl-1-amino-1-cyclopentanecarboxylate

To a dimethylformamide (25 ml) solution of ethyl 1-amino-1-cyclopentanecarboxylate liberated from its hydrochloride (1.0 g, 5 mmoles) with N-ethylpiperidine (0.7 ml) there was portionwise added benzyloxycarbonylalanyl-glycine p-nitrophenyl ester (2.1 g, 5 mmoles). After 3 hours of stirring and 12 hours of standing at room temperature the solution was evaporated, the residue was taken into ethyl acetate and extracted successively with 1% ammonia and water, dried over anhydrous sodium sulfate and evaporated. The residue was crystallized from ethyl acetate-petroleum ether to give 1.4 g (67%) of the title product, m.p. 119° to 121° C. An analytical sample was crystallized similarly, m.p. 137° to 139° L C. $[\alpha]_D^{20}-3.4°$.

Hydrogenolytic deprotection of this compound similarly as described in Example 1 yielded ethyl alanyl-glycyl-1-amino-1-cyclopentanecarboxylate, citrate $R_f$ 0.28/$S_1$, 0.71/$S_2$. $[\alpha]^{20}+7.3°$.

$R_f$ and optical rotations always e.g.: $R_f$ 0.28/$S_1$, 0.71/$S_2$ $[\alpha]^{20}+7.3°$ (here only +).

Although the invention is described and illustrated with reference to a plurality of embodiments thereof, it is to be expressly understood that it is in no way limited to the disclosure of such preferred embodiments but is capable of numerous modifications within the scope of the appended claims.

We claim:
1. Peptide derivatives of the general formula I,

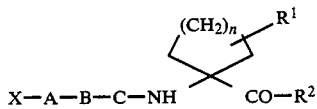

in which
X is H, a $C_2$ to $C_5$ alkanecarbonyl, a $C_3$ to $C_6$ carboxyalkanecarbonyl or a p-toluenesulfonyl,
A is a glycine, alanine, leucine, phenylalanine, tyrosine, lysine or arginine residue,
B is a glutamine, proline, arginine or lysine residue or a direct chemical bond,
n is an integer of from 1 to 3, $R^1$ is H or a $C_1$ to $C_3$ alkyl and $R^2$ is a $C_1$ to $C_3$ alkoxyl or an amino group selected from the group consisting of glycine, alanine, leucine, phenylalanine and serine when C is a glycine, alanine, leucine, phenylalanine, glutamine or serine residue or
$R^2$ is a glycine, alanine, leucine, phenylalanine or serine methyl ester, ethyl ester or amide residue when C is a direct chemical bond, and pharmaceutically acceptable acid addition salts thereof.
2. Ethyl, leucyl-alanyl-1-amino-1-cyclopentanecarboxylate and its citrate.
3. Ethyl, alanyl-alanyl-1-amino-1-cyclopentanecarboxylate and its citrate.
4. Methyl, alanyl-alanyl-1-amino-1-cyclobutanecarboxylate and its citrate.
5. Ethyl, alanyl-alanyl-1-amino-1-cyclohexanecarboxylate and its citrate.
6. Ethyl, phenylalanyl-phenylalanyl-1-amino-1-cyclopentanecarboxylate and its citrate.
7. Ethyl, glycyl-prolyl-alanyl-1-amino-1-cyclopentanecarboxylate and its citrate.
8. Ethyl, 3-carboxypropionylphenylalanyl-phenylalanyl-1-amino--cyclopentanecarboxylate.
9. Ethyl, N-acetyltyrosyl-alanyl-1-amino-1-cyclopentanecarboxylate.
10. Ethyl, acetylleucyl-lysyl-glutaminyl-1-amino-1-cyclopentanecarboxylate and its acetate.
11. Ethyl, acetylleucyl-lysyl-glycyl-1-amino-1-cyclopentanecarboxylate and its acetate.
12. N-Acetyltyrosyl-1-amino-1-cyclopentanecarbonylserine methyl ester.
13. Ethyl, alanyl-glycyl-1-amino-1-cyclopentanecarboxylate and its citrate.
14. Ethyl, acetylleucyl-arginyl-alanyl-1-amino-1-cyclopentanecarboxylate and its acetate.
15. Methyl, acetylleucyl-lysyl-alanyl-1-amino-1-cyclopentanecarboxylate and its acetate.

* * * * *